United States Patent [19]

Abraham et al.

[11] Patent Number: 4,520,203

[45] Date of Patent: May 28, 1985

[54] RESOLUTION OF (±)-1,8-DIETHYL-1,3,4,9-TETRAHYDROPYRANO[3,4-B]INDOLE-1-ACETIC ACID USING CINCHONINE

[75] Inventors: Nedumparambil A. Abraham, Dollard-des-Ormeaux; Christopher A. Demerson, Montreal, both of Canada

[73] Assignee: American Home Products Corporation, New York, N.Y.

[21] Appl. No.: 523,987

[22] Filed: Aug. 16, 1983

[51] Int. Cl.³ .......................................... C07D 493/04
[52] U.S. Cl. ..................................... 548/432; 546/134
[58] Field of Search ....................... 548/432; 546/134

[56] References Cited

U.S. PATENT DOCUMENTS

| | | | |
|---|---|---|---|
| 3,939,178 | 2/1976 | Demerson et al. | 548/432 |
| 3,988,365 | 10/1976 | Gallegra | 546/134 |
| 4,118,394 | 10/1978 | Demerson et al. | 548/432 |
| 4,230,860 | 10/1980 | Raghu | 546/134 |
| 4,399,284 | 8/1983 | Cannata et al. | 546/134 |

OTHER PUBLICATIONS

Merck Index, 9th Edition, pp. 295, 2276.
Demerson et al., J. Med. Chem., 18, 189 (1975).

*Primary Examiner*—Donald G. Daus
*Assistant Examiner*—Cecilia Shen

[57] ABSTRACT

Racemic (±)-1,8-diethyl-1,3,4,9-tetrahydropyrano[3,4-b]indole-1-acetic acid is resolved with cinchonine to obtain directly the pure salt of the (+)-enantiomer with cinchonine and converting the latter salt to the pure (+)-enantiomer.

3 Claims, No Drawings

RESOLUTION OF (±)-1,8-DIETHYL-1,3,4,9-TETRAHYDROPYRANO[3,4-B]INDOLE-1-ACETIC ACID USING CINCHONINE

BACKGROUND OF THE INVENTION

This invention relates to a process for resolving (±)-1,8-diethyl-1,3,4,9-tetrahydropyrano[3,4-b]indole-1-acetic acid using cinchonine to obtain the corresponding (+)-enantiomer.

(±)-1,8-Diethyl-1,3,4,9-tetrahydropyrano[3,4-b]indole-1-acetic acid, an optically inactive racemic mixture, is known generically as etodolic acid or etodolac and is well known as an anti-inflammatory and analgesic agent, C. A. Demerson et al., U.S. Pat. No. 3,939,178, issued Feb. 17, 1976; and C. A. Demerson et al., J. Med. Chem., 18, 189 (1975) and 19, 391 (1976).

The resolution of racemic organic acids is unpredictable. Attempts to resolve etodolac have been plagued with numerous problems, for example, crystallization of the wrong enantiomer, selection of an appropriate base for forming the diastereoisomeric salt, low yields, multiple crystallizations and time consumption.

The herein described process avoids the above problems and the (+)-enantiomer is obtained in high yield and in a commercially feasible operation.

DESCRIPTION OF THE INVENTION

The process for preparing (+)-1,8-diethyl-1,3,4,9-tetrahydropyrano[3,4-b]indole-1-acetic acid comprises: dissolving one part by weight of (±)-1,8-diethyl-1,3,4,9-tetrahydropyrano[3,4-b]indole-1-acetic acid and about 1.1 to 1.3 parts by weight of cinchonine in about 40 to 60 parts by weight of methanol at about 50° to 65° C.; cooling the solution to crystallize the corresponding salt of (+)-1,8-diethyl-1,3,4,9-tetrahydropyrano[3,4-b]indole-1-acetic acid with cinchonine; dissolving the latter salt in a mixture of a water-immiscible organic solvent and an aqueous mineral acid; separating the water-immiscible organic solvent; and isolating substantially pure (+)-1,8-diethyl-1,3,4,9-tetrahydropyrano[3,4-b]indole-1-acetic acid from the water-immiscible organic solvent.

The salt of (+)-1,8-diethyl-1,3,4,9-tetrahydropyrano[3,4-b]indole-1-acetic acid with cinchonine is preferably crystallized from the solution at about 10° to 25° C.

Suitable water-immiscible organic solvents include toluene, benzene, ethyl acetate and the like. Ethyl acetate is preferred.

Suitable aqueous mineral acids include about 1 to 6 normal hydrochloric acid, sulfuric acid, phosphoric acid and the like. Hydrochloric acid is preferred.

An important feature of the present process is that the salt of the (+)-enantiomer with cinchonine is obtained substantially pure by direct crystallization from the first step of this process and that further purification of this salt by recrystallization is not required. Furthermore, only one crystallization of the free (+)-enantiomer acid is sufficient to obtain the pure (+)-enantiomer. All these features avoid the expensive and tedious operations of purification procedures usually required for resolution and serve to promote the efficiency of the present process.

The anti-inflammatory and analgesic activity of (+)-1,8-diethyl-1,3,4,9-tetrahydropyrano[3,4-b]indole-1-acetic acid is determined by the methods described in the above cited U.S. Pat. No. 3,939,178. How to use and pharmaceutical formulations are also described in the patent. The useful anti-inflammatory and analgesic activity of the racemic mixture has been found to reside only in the (+)-enantiomer.

The following examples illustrate further this invention.

EXAMPLE 1

(+)-1,8-Diethyl-1,3,4,9-tetrahydropyrano[3,4-b]indole-1-acetic Acid

A solution of (±)-1,8-diethyl-1,3,4,9-tetrahydropyrano[3,4-b]indole-1-acetic acid (20 g, 0.070 mol) in methaol (150 mL) was added to a hot solution of cinchonine (22.2 g, 0.075 mol) in methanol (1200 mL). The clear solution was left at room temperature overnight. The first crop of crystals weighed 19 g. The mother liquor was concentrated to 350 mL and allowed to crystallize overnight to give a second crop (2.2 g) of crystals. This salt (21.2 g) was suspended in ethyl acetate (100 mL) and stirred while aqueous dilute hydrochloric acid was added until the lower layer was very acidic. The ethyl acetate layer was separated. The aqueous layer was extracted again with ethyl acetate (100 mL). The organic layers were washed with aqueous brine, dried over $Na_2SO_4$ and concentrated to 20 mL. Hexane (40 mL) was added and the clear solution was allowed to crystallized to give the title compound (8.1 g): mp 140°–142° C., and $[\alpha]_D +47.9°$ (c=1, isopropanol).

EXAMPLE 2

Effect on Primary Inflammation of Adjuvant Induced Arthritis

The method used was a modification of that described by J. Wax et al., J. Pharmac. Exp. Ther., 192,166 (1975). Groups of rats were injected intradermally in the left hindpaw (injected hindpaw) with 0.1 mL of a fine suspension of killed and dried Mycobacterium butyricum (Difco) at a concentration of 5 mg/mL in liquid paraffin (Freund's complete adjuvant). Drugs were administered immediately before the adjuvant, 24 h and 48 h after the adjuvant (day 0,1 and 2). The injected hindpaw volume was measured before the adjuvant and 24 after the last drug administration (day 3). The difference between the hindleg volume before the adjuvant injection and the day 3 reading represented the edema volume. Rats showing an inhibition of hindpaw edema of 25% or more when compared to the mean edema volume of the control group (10 rats) were considered to exhibit an anti-inflammatory effect. The dose which produced a positive effect in half the rats ($ED_{50}$) was calculated by probit analysis (D. J. Finney, Statistical Method in Biological Assay, MacMillan, New York, 1978). There was 10 to 20 rats per dose and 4 dose levels were used. An adjuvant-injected control group receiving water only was also included. Hindleg volume was determined by a mercury displacement method. Hindlegs were dipped in mercury up to the hairline and the amount displaced was read in grams on a direct reading balance. It represented the volume of the hindleg (13.6 g of mercury=1 mL). Male Charles River albino rats weighing 180 to 200 g were used. The results are expressed $ED_{50}$'s, the dose which reduced, by 25L % the edema of primary adjuvant arthritis in 50% of the rats. In this model the $ED_{50}$ for (+)-1,8- diethyl-1,3,4,9-tetrahydropyrano[3,4-b]indole-1-acetic acid was 0.7±0.3 mg/kg, while the (−)-enantiomer was inactive. The ED$_{50}$ of the (±)-racemate in this test was 1.1±0.5 mg/kg.

We claim:

1. A process for preparing (+)-1,8-diethyl-1,3,4,9-tetrahydropyrano[3,4-b]indole-1-acetic acid, which comprises dissolving one part by weight of (±)-1,8-diethyl-1,3,4,9-tetrahydropyrano[3,4-b]indole-1-acetic acid and about 1.1 to 1.3 parts by weight of cinchonine in about 40 to 60 parts by weight of methanol at about 50° to 65° C.; cooling the solution to crystallize the corresponding salt of (+)-1,8-diethyl-1,3,4,9-tetrahydropyrano[3,4-b]indole-1-acetic acid with cinchonine; dissolving the latter salt in a mixture of water-immiscible organic solvent and an aqueous mineral acid; separating the water-immiscible organic solvent; and isolating substantially pure (+)-1,8-diethyl-1,3,4,9-tetrahydropyrano[3,4-b]indole-1-acetic acid from the water-immiscible organic solvent.

2. The process of claim 1 wherein the water-immiscible organic solvent is ethyl acetate and the aqueous mineral acid is hydrochloric acid.

3. The process of claim 2 wherein the salt of (+)-1,8-diethyl-1,3,4,9-tetrahydropyrano[3,4-b]indole-1-acetic acid with cinchonine is crystallized from the solution at about 10° to 25° C.

* * * * *